United States Patent
Suga

(10) Patent No.: US 6,994,696 B2
(45) Date of Patent: Feb. 7, 2006

(54) INDIVIDUAL PACKAGE OF BODY FLUID ABSORBENT ARTICLE

(75) Inventor: Ayami Suga, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 370 days.

(21) Appl. No.: 10/267,160

(22) Filed: Oct. 9, 2002

(65) Prior Publication Data

US 2003/0073970 A1 Apr. 17, 2003

(30) Foreign Application Priority Data

Oct. 17, 2001 (JP) ............................. 2001-319141

(51) Int. Cl.
*A61F 13/20* (2006.01)
(52) U.S. Cl. ........................... 604/385.02; 604/385.13; 604/14
(58) Field of Classification Search ............ 604/11–18, 604/385.02, 385.13, 385.19
See application file for complete search history.

(56) References Cited

U.S. PATENT DOCUMENTS

| 4,182,336 A | * | 1/1980 | Black .................... 604/385.13 |
| 4,605,403 A | * | 8/1986 | Tucker .................. 604/385.13 |
| 4,973,302 A | * | 11/1990 | Armour et al. ............... 604/15 |
| 6,299,607 B1 | * | 10/2001 | Osborn et al. ......... 604/385.02 |

FOREIGN PATENT DOCUMENTS

| JP | 61-115525 | 7/1986 |
| JP | 07-323045 | 12/1995 |

* cited by examiner

*Primary Examiner*—Tatyana Zalukaeva
*Assistant Examiner*—C. Lynne Anderson
(74) *Attorney, Agent, or Firm*—Darby & Darby

(57) ABSTRACT

An individual package of a body fluid absorbent article can instantly take care of used body fluid absorbent article without staining fingers with a used substance disposing sheet immediately after opening the package upon changing the body fluid absorbent article. In the individual package of a body fluid absorbent article, a used substance disposing sheet to be used for wrapping a used absorbent body taken out from a user's body for disposal, is packed within the individual package together with the body fluid absorbent article. The package sheet is provided with a cutting portion for separating the packaging bag into bag fractions. A part of the used substance disposing sheet is fixed to one of the bag fractions.

14 Claims, 10 Drawing Sheets

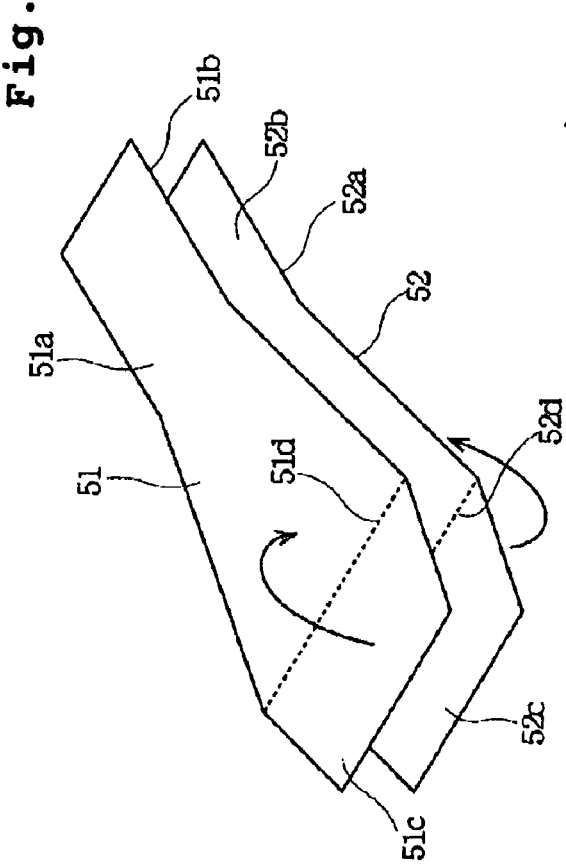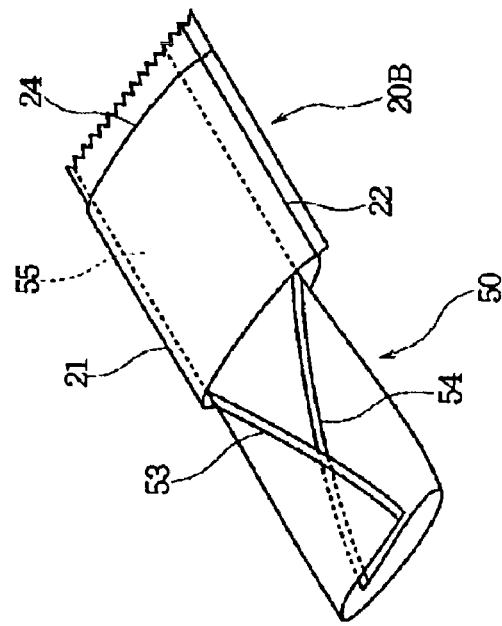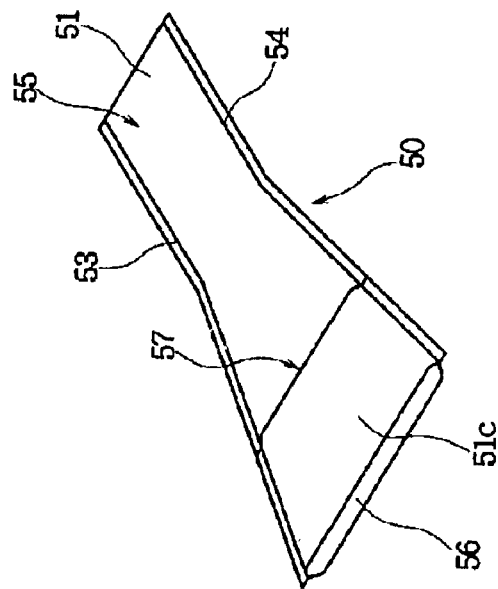

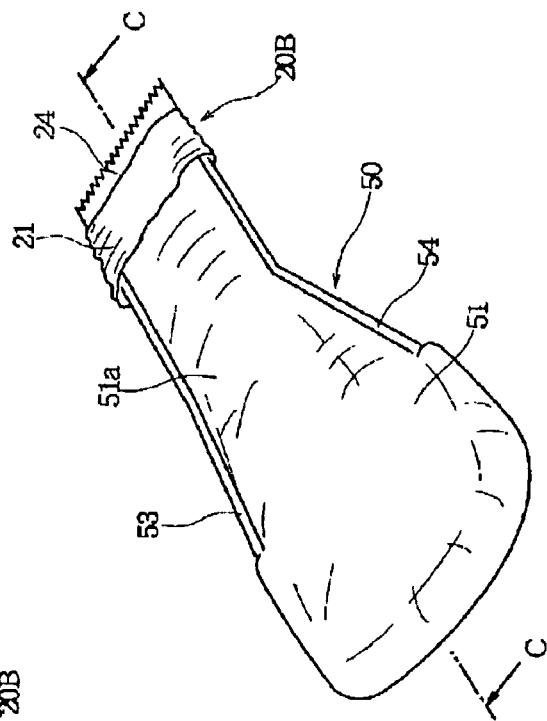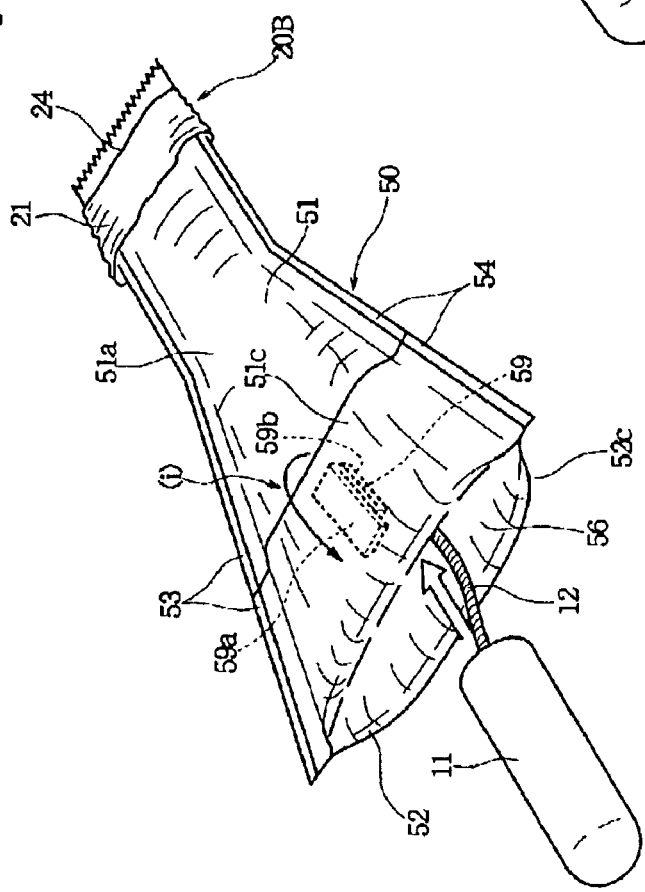

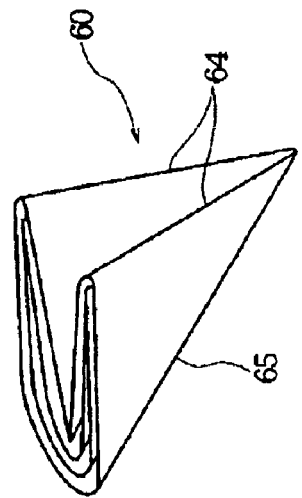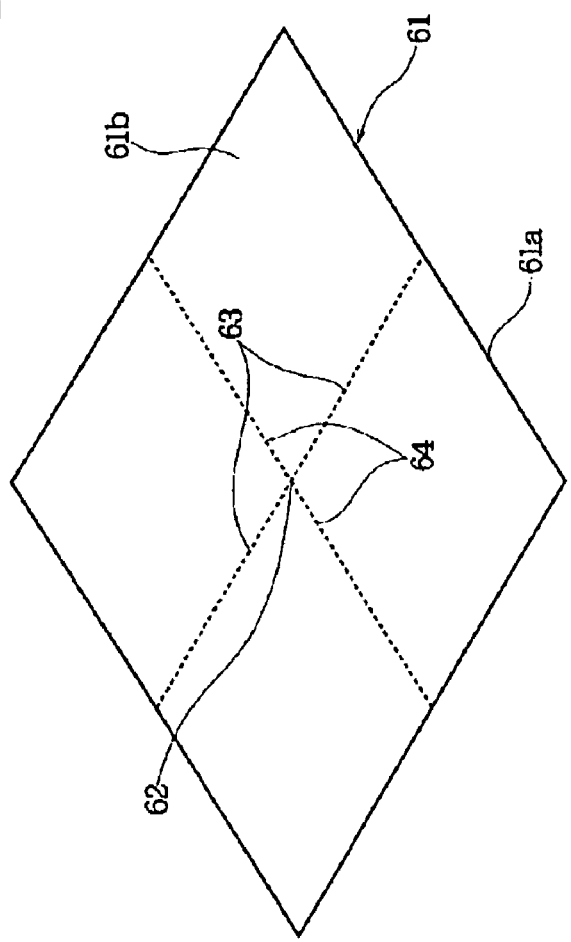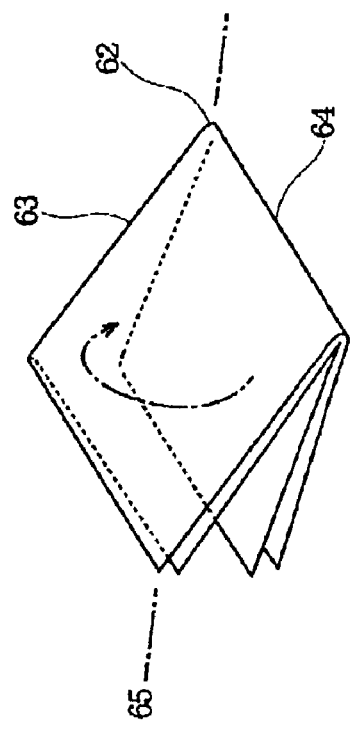
Fig. 9A
Fig. 9B
Fig. 9C

INDIVIDUAL PACKAGE OF BODY FLUID ABSORBENT ARTICLE

BACKGROUND OF THE INVENTION

1. Field of the Invention

The present invention relates generally to an individual package of a body fluid absorbent article such as a sanitary tampon assembly in which the body fluid absorbent article including an absorbent body to be inserted into a vagina is individually packed into the individual package. More particularly, the invention relates to an individual package of a body fluid absorbent article which permits easy disposal of used absorbent article without contamination of user's hand after opening the package.

2. Description of the Related Art

Conventionally marketed sanitary tampon assembly include an applicator type sanitary tampon having the absorbent body (also referred to as a tampon) received within an applicator and to be inserted into user's body cavity (vagina) by means of the applicator, and a finger type sanitary tampon having the absorbent body (also referred to as a tampon) to be inserted into user's body cavity by user's fiber without using the applicator. The applicator type sanitary tampon is individually packed within an individual package bag in a condition where the tampon is received within the applicator to form the individual package. Then, a plurality of individual packages are packed into a box as a product package, and the product packages are put into market.

Upon changing to new one, the tampon on use is taken out from the user's body cavity. Then, the used tampon is wrapped with a plurality of plies of toilet papers or tissue papers for disposal. Then, the new individual package of the tampon applicator assembly is opened to take out and insert new tampon into the user's body cavity, i.e. vagina.

On the other hand, a package of the sanitary tampon disclosed in Japanese Unexamined Utility Model Publication No. Showa 61-115525, includes a first bag, in which not yet used sanitary tampon is sealingly enclosed, and a second bag which does not contain the sanitary tampon and is joined with the first bag across a perforation for separation therealong. The user at first takes out the used tampon from the body cavity and puts the used tampon into the second bag. Then, an opening end of the second bag is closed by a closure portion applied an adhesive for disposal. Thereafter, the first bag is opened for inserting new tampon into the body cavity.

On the other hand, Japanese Unexamined Patent Publication No. Heisei 7-323045 discloses a sanitary napkin package, in which a paper is packed together with a sanitary napkin. Upon changing the sanitary napkin, the package is opened to take out the sanitary napkin together with the paper. Then, the user's crotch part may be wiped off by the paper, and then the new sanitary napkin is fit on the user's body.

In case of the sanitary tampon disclosed in Japanese Unexamined Utility Model Publication No. Showa 61-115525, since the used tampon can be disposed by putting and sealing into the second bag, user's hand will not be stained by the used tampon thereafter. However, until the tampon taken out from the body cavity is enclosed in the second bag, the user is required to grip the used tampon by fingers directly or via a toilet paper or tissue paper to put into the second bag to potentially stain the fingers.

On the other hand, upon taking out the tampon from the body cavity, a take-out cord extending from the absorbent body is gripped via the toilet paper to pull out the tampon. At this time, menstrual blood depositing on the take-out cord may deposit on the fibers to stain. On the other hand, upon gripping the take-out cord lead out the body cavity by the fingers via the toilet paper, difficulty is encountered in perceiving the take-out cord to quickly grip the take-out cord.

On the other hand, in the package disclosed in Japanese Unexamined Patent Publication No. Heisei 7-323045, the paper is contained in the package. However, when the package is opened and the sanitary napkin is taken out, the paper may be unwantedly drawn out together with the sanitary napkin to drop off to be difficult to use. On the other hand, there is also disclosed that the paper is connected to the sanitary napkin, and is cut away from the sanitary napkin upon use. However, it is troublesome to cut away the paper from the sanitary napkin. On the other hand, the structure where the paper is connected to the sanitary napkin before use is not natural to be poorly practical.

Furthermore, since what is contained in the package together with the sanitary napkin is paper in the package disclosed in Japanese Unexamined Patent Publication No. Heisei 7-323045, if the used sanitary napkin or the used tampon is wrapped by the paper, menstrual blood may permeate therethrough.

SUMMARY OF THE INVENTION

The present invention has been worked out in view of the shortcoming in the prior art set forth above. It is therefore an object of the present invention to provide an individual package of a body fluid absorbent article which can instantly take care of used body fluid absorbent article without staining fingers with a used substance disposing sheet immediately after opening the package upon changing the body fluid absorbent article.

According to one aspect of the present invention, an individual package of a body fluid absorbent article, individually packing the body fluid absorbent article containing an absorbent body to be inserted into a vagina with a package sheet in a form of packaging bag, wherein a used substance disposing sheet for wrapping a used absorbent body taken out from a user's body for disposal, is packed within the individual package together with the body fluid absorbent article, the package sheet is provided with a cutting portion for separating the packaging bag into bag fractions, and a part of the used substance disposing sheet is fixed to one of the bag fractions.

In the individual package, when the packaging bag is sheared at the cutting portion, the used substance disposing sheet is fixedly joined with the separated bag fraction. Therefore, a user may obtain the used substance disposing sheet immediately after opening the package. Therefore, it becomes possible to grip the take-out code to take out the used absorbent body from the user's body, and instantly wrap the used tampon with the used substance disposing sheet.

For example, the packaging bag is preferably a longitudinally elongated shape, the packaging bag may be provided with the cutting portion for separating into a first bag fraction and a second bag fraction, and the used substance disposing sheet may be fixed in the second bag fraction and extended from the second bag fraction.

The used substance disposing sheet is of the size extending from the second bag fraction after separating the packaging bag. The used substance disposing sheet can be easily stretched to facilitate putting the used absorbent body.

The used substance disposing sheet may be welded together with the package sheet in a condition sandwiched by the package sheet at a longitudinal end of the second bag fraction.

Since the used substance disposing sheet is welded at the end portion together with the package sheet, it becomes unnecessary to provide separate means for fixing the used substance disposing sheet to facilitate manufacturing.

The body fluid absorbent article may include the absorbent body and a take-out cord extending from a rear end of the absorbent body. In the alternative, the body fluid absorbent article may include the absorbent body, a take-out cord extending from the rear end of the absorbent body and an applicator having an outer cylinder receiving therein the absorbent body and an inner cylinder along which the take-out cord is inserted, and which is inserted into the outer cylinder for pushing the absorbent body out of the outer cylinder. The outer cylinder of such body fluid absorbent article may be contained in the first bag fraction.

Since the absorbent body or the outer cylinder of the applicator is contained in the first bag fraction, the non-use absorbent body or the outer cylinder of the applicator can be kept in sanitary condition as contained in the first bag fraction while the used absorbent body or the like is wrapped for disposal with the second bag fraction.

The used substance disposing sheet may be formed into a cylindrical disposing bag. In this case, a diameter of the cylindrical disposing bag as stretched may be greater than a diameter of the second bag fraction, and the cylindrical disposing bag may be received within the packaging bag in folded condition. In the alternative, the cylindrical disposing bag may have a diameter at an opening portion of the cylindrical disposing bag extending from the second bag fraction, greater than a diameter of a portion positioned within the second bag fraction.

When the used substance disposing sheet is a cylindrical disposing bag, the used absorbent body can be disposed with wrapping in the cylindrical disposing bag. On the other hand, the opening portion of the cylindrical disposing bag is expanded to make the diameter greater, so that the used absorbent body can be easily wrapped in the cylindrical disposing bag.

In the further alternative, the cylindrical disposing bag extending from the second bag fraction, may have a folded back portion folded outwardly at the opening portion for defining a finger pocket portion defined between the folded back portion and an outer surface of the cylindrical disposing bag.

In the shown example, the used tampon including the absorbent body and the take-out code can be gripped on the inner surface of the cylindrical disposing bag by inserting fingers into the finger pocket portion to hardly stain the user's hand. Furthermore, by returning the folded back portion to the original position after wrapping the used tampon in the cylindrical disposing bag, the used tampon can be completely enclosed within the cylindrical disposing bag.

The used substance disposing sheet may be folded along folding lines radially extending from an arbitrarily set folding center, and the used substance disposing sheet is fixed onto an inner surface of the package sheet at the folding center or a portion in the vicinity of the folding center.

When the used substance disposing sheet is fixed on the inner surface of the package sheet, the used substance disposing sheet can be stretched to widen after opening the package.

In the alternative embodiment, the used substance disposing sheet may be rolled and a part of the rolled used substance disposing sheet may be fixed onto an inner surface of the package sheet.

The packaging bag may define a space for receiving the body fluid absorbent article and a space separated from the former space and receiving the used substance disposing sheet.

The used substance disposing sheet has a liquid blocking function.

By providing liquid blocking function for the used substance disposing sheet, stain of the fingers of the user is hardly caused upon griping the withdrawing cord or the used absorbent body with the used substance disposing sheet.

Also, one surface side of the used substance disposing sheet may be formed with a fibrous structure having water absorbing function. For example, it is preferred that the inner surface of the cylindrical disposing body is formed from the fibrous structure.

By wrapping the used absorbent body by the surface of the used substance disposing sheet having water absorbing function, liquid eluding from the absorbent body can be absorbed by the fibrous structure to eliminate or reduce possibility of external leakage of the liquid.

The individual package of a body fluid absorbent article may further include fastening means for retaining the used substance disposing sheet wrapping the used absorbent body in closed condition.

By maintaining the used substance disposing sheet in closed condition by the fastening means, leakage of the body fluid, such as menstrual blood, absorbed by the absorbent body from leaking out of the used substance disposing sheet.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings:

FIGS. 7A, 7B and 7C are perspective views showing a process forming another construction of the cylindrical disposing bag;

FIG. 8A is a perspective view showing a condition where a tampon is received in the cylindrical disposing bag shown in FIGS. 7A, 7B and 7C;

FIG. 8B is a perspective view showing a condition where an opening portion of the cylindrical disposing bag is closed;

FIG. 8C is a section taken along line C-C of FIG. 8B;

FIGS. 9A, 9B and 9C are perspective views showing a further embodiment of the process of folding the used substance disposing sheet;

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
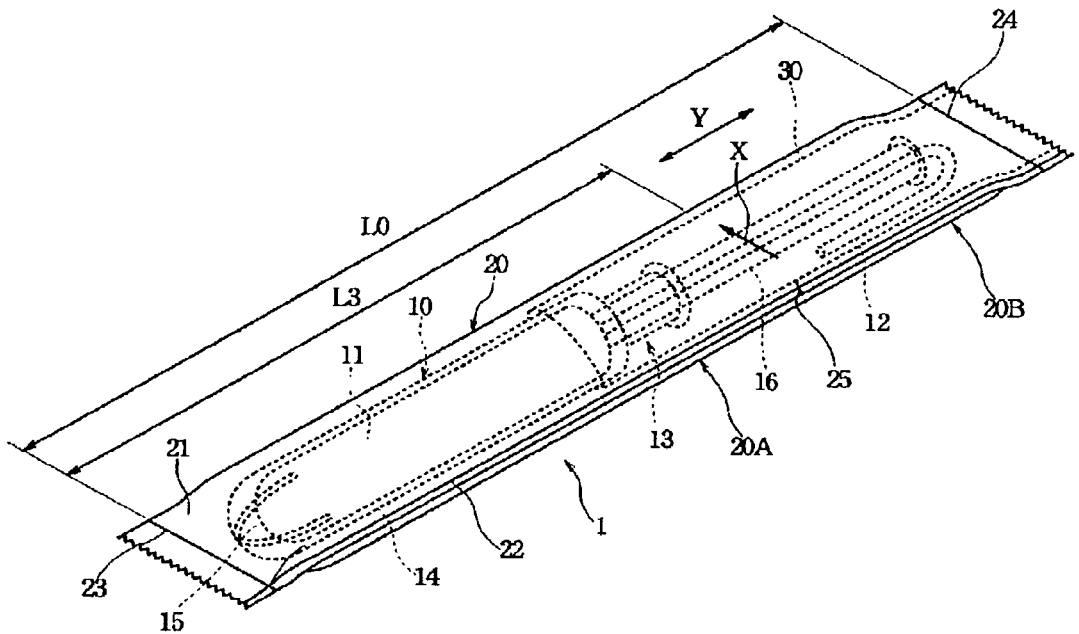
FIG. 1 is a perspective view showing the preferred embodiment of an individual package of a body fluid absorbent article according to the present invention.
Figure 2A:
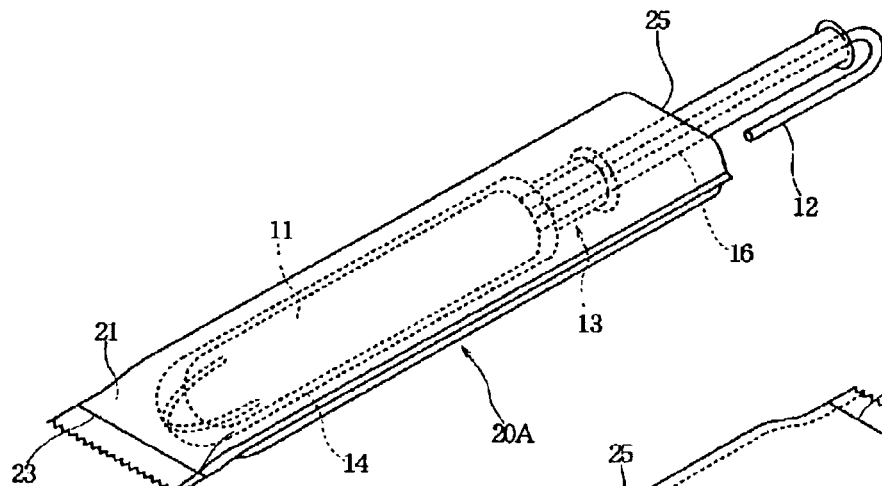
FIG. 2A is a perspective view showing a first bag fraction after separation.
Figure 2B:
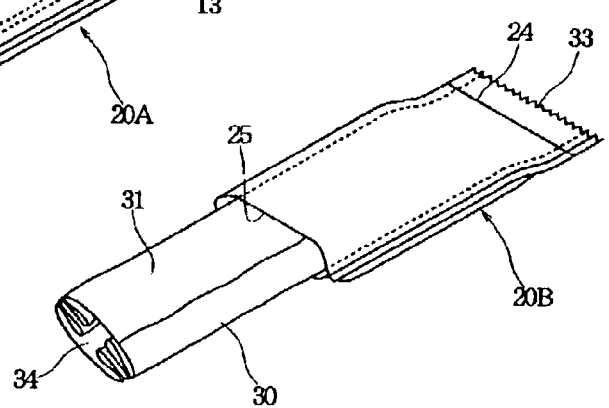
FIG. 2B is a perspective view showing a second bag fraction.

FIG. 1 is a perspective view showing the preferred embodiment of an individual package of a body fluid absorbent article according to the present invention, FIG. 2A is a perspective view showing a first bag fraction after separation, and FIG. 2B is a perspective view showing a second bag fraction.

As one example of the body fluid absorbent article, the individual package of the applicator type sanitary tampon (hereinafter referred to as a sanitary tampon) will be described hereinafter.

An individual package 1 shown in FIGS. 1, 2A and 2B is formed by packing each individual sanitary tampon 10 in a packaging bag 20.

In the shown embodiment, the sanitary tampon 10 is formed with a tampon including an absorbent body 11 and a take-out cord 12 extending from a rear end of the absorbent body, and an applicator 13 housing the tampon.

The absorbent body 11 is formed by compressing a hydrophilic fiber, such as cotton, rayon and so forth for forming a fibrous shaped absorbent core, and wrapping the fibrous shaped absorbent core with a liquid permeable sheet, such as non-woven fabric and so forth. When the absorbent body 11 is inserted into a vagina of lady on menstruation, the absorbent body 11 absorbs menstrual blood to expand in vagina. While the absorbent body 11 is retained in the vagina, the take-out cord 12 is lead out of the lady's body through vaginal introitus. By pulling the take-out cord 12, the used absorbent body 11 can be taken out from vagina.

The applicator 13 is formed of a synthetic resin material, and has an outer cylinder 14 receiving the absorbent body 11 and an inner cylinder 16 opposing to a rear end of the absorbent body 11 and being slidable relative to the outer cylinder 14. On a tip end portion of the outer cylinder 14, a plurality of elastically openable claws 15 are formed integrally in mutually separated form. On the other hand, the take-out cord 12 extending from the rear end of the absor-bent body 11 is inserted into the inner cylinder 16 and extended rearwardly from a rear end of the inner cylinder 16.

Particular construction of the sanitary tampon as the body fluid absorbent article has been disclosed in commonly owned U.S. Pat. No. 6,432,075, to Wada et al., and commonly owned co-pending U.S. Pat. No. 6,432,076 to Wada et al. The disclosures of the above-identified U.S. Patent and the co-pending U.S. Patent are herein incorporated by reference.

When the sanitary tampon 10 is used, the outer cylinder 14 carrying the inner cylinder 16 is inserted into the vagina through the vaginal introitus. Then, the inner cylinder 16 is pushed inwardly along the outer cylinder 14. During inward motion of the inner cylinder 16, the absorbent body 11 is pushed out of the outer cylinder 14 with elastically opening the claws 15 at the tip end of the outer cylinder 14. Thus, the absorbent body 11 is inserted into the vagina.

The packaging bag 20 is formed from a package sheet 21. In the shown embodiment, the package sheet 21 is formed from polyethylene film. In place of polyethylene film, polypropylene film, paper material, a laminate material of polyethylene film and paper material may also be used.

The packaging bag 20 is formed into so-called pillow type package form. Namely, in manufacturing the packaging bag, a continuous polyethylene film in stripe form is sealed along a longitudinally extending seal portion 22 to form into cylindrical disposing bag. The sanitary tampon 10 is inserted into the cylindrical disposing bag. Then, one end of the cylindrical disposing bag corresponding to one (front) end portion of the sanitary tampon 10 is sealed in a direction substantially perpendicular to the longitudinally extending seal portion 22 to form a laterally extending seal portion 23. Also, on the other end of the cylindrical disposing bag corresponding to the other (rear) end portion of the sanitary tampon 10 is sealed in the direction substantially perpendicular to the longitudinally extending seal portion 22 to form a laterally extending seal portion 24. Between the laterally extending seal portions 23 and 24, the package sheet 21 is cut to form the independent individual package 1.

At the central portion of the packaging bag 20, a cutting portion 25 for shearing the packaging bag 20 into two fractions in longitudinal direction (Y direction) is formed. In case of the embodiment shown in FIG. 1, the package sheet 21 is formed from a resin film elongated in lateral direction perpendicular to the longitudinal direction (Y direction). Also, in the edge portion of the package sheet 21 laterally extending from the longitudinally extending seal portion 22, a thumb index to be a trigger in forming a cut line is formed. This thumb index serves as the cutting portion 25. With taking the thumb index as trigger, the package sheet is sheared to propagate the cut line in the lateral direction of the packaging bag 20 as shown by arrow X. Thus, the package sheet 21 can be easily cut.

In the alternative, an unpacking tape may be bonded on the outer surface or the inner surface of the package sheet 21 in a direction of arrow X by adhesive or by heat seal. The unpacking tape may be extended over the entire circumference of the packaging bag 20 in the lateral direction substantially perpendicular to the longitudinal direction. In the further alternative, the unpacking tape may be fixed on a part of the packaging bag 20. An end portion of the tape is extended outside of the packaging bag 20. Upon unpacking the individual package of the sanitary tampon, the user may grip the end portion of the tape and pull the tape in the X direction. Then, the package sheet 21 is progressively cut by the unpacking tape so that the package sheet can be easily cut.

In the alternative, the cutting portion 25 may be a perforation formed in the circumferential direction of the packaging bag 20 so as to shear the package sheet 21 of the packaging bag 20 in circumferential direction.

By cutting the packaging bag 20 at the cutting portion 25, the packaging bag 20 is separated into a first bag fraction 20A shown in FIG. 2A and a second bag fraction 20B shown in FIG. 2B. The absorbent body 11 and the outer cylinder 14 in which the absorbent body is received, are placed within the first bag fraction 20A. The take-out cord 12 and the inner cylinder 16 are located at the position in the second bag fraction 20B before separation into the first and second bag fractions 20A and 20B, and are projected when the second bag fraction 20B is separated away from the first bag fraction 20A.

On the other hand, in the second bag fraction 20B as separated away from the first bag fraction 20A, a cylindrical disposing bag 30 formed from a used substance disposing sheet 31 is received.

Figure 3A:
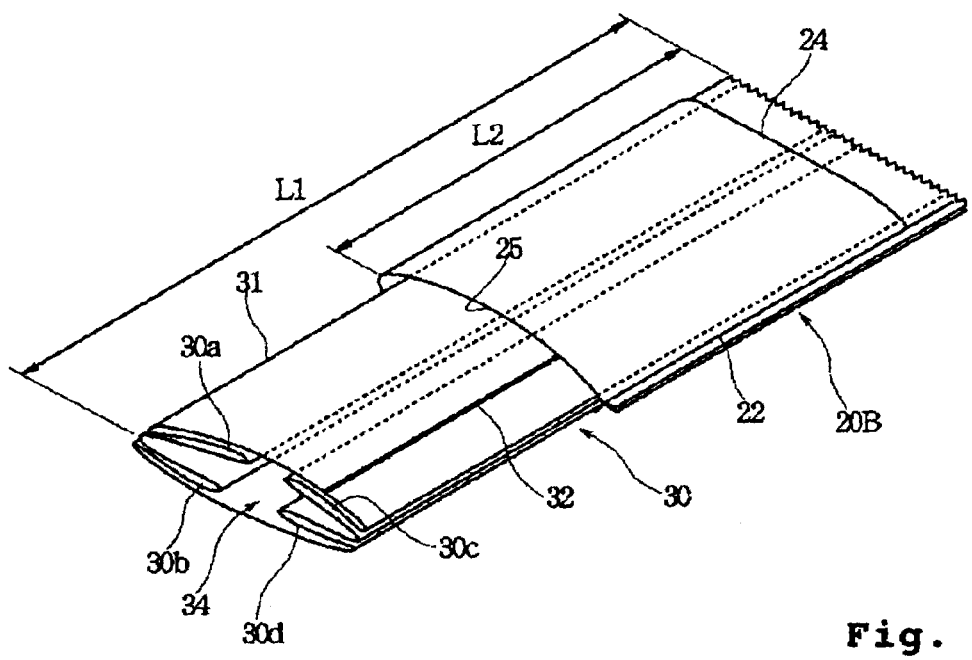
FIG. 3A is a perspective view showing a packaging bag of a second bag fraction and a used substance disposing sheet.
Figure 3B:
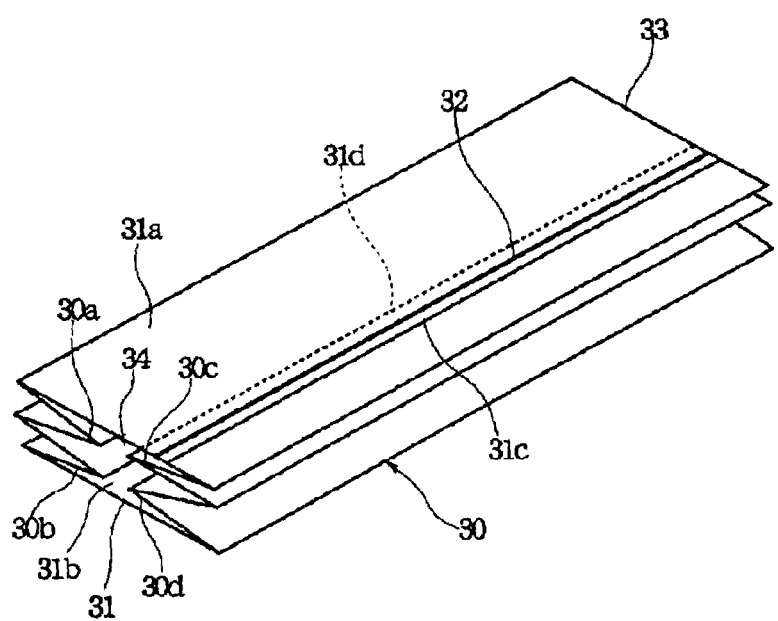
FIG. 3B is a perspective view showing a cylindrical disposing bag.

FIG. 3A is a perspective view showing a packaging bag of a second bag fraction and a used substance disposing sheet, and FIG. 3B is a perspective view showing the structure of a cylindrical disposing bag.

The used substance disposing sheet 31 has a first layer 31a located outer side of the cylindrical disposing bag 30 and having an externally directed-outer surface, and a second layer 31b located inside of the cylindrical disposing bag 30 and having an internally directed inner surface. In order to provide liquid blocking function for the used substance disposing sheet 31, the first layer 31a is formed from a resin film such as polyethylene film, polypropylene film and the like, or in the alternative, formed from a non-woven fabric provided water repellent treatment.

The second layer 31b is formed from a fibrous structure fulfilling water absorbing function. The fibrous structure is required to have heat fusing ability and water absorbing function. Therefore, the fibrous structure may be formed from non-woven fabric fabricated with polyethylene, polypropylene and the like and provided with hydrophilic treatment by spun-bonding process, or non-woven fabric fabricated with single fibers of polyethylene, polypropylene or with a bicomponent synthetic fiber having sheath-core structure of sheath portion formed of polyethylene and core portion formed of polypropylene or polyester and provided hydrophilic treatment by through-air bonding process or spunlace process. In the alternative, non-woven fabric fabricated by spun-bonding process and blended with hydrophilic fibers such as rayon, pulp or the like may also be used as the fibrous structure.

The resin film forming the first layer 31a and the fibrous structure forming the second layer 31b are integrally laminated by adhering means using an adhesive, heat-fusing means and so forth. In the alternative, the resin film and the fibrous structure may be laminated by extruding a molten resin on one side of the fibrous structure.

As shown in FIG. 3B, in the condition where end edge portions 31c and 31d of the used substance disposing sheet 31 are stacked, the stacked portion is heat sealed along a seal line 32 extending in the longitudinal direction to form the cylindrical disposing bag 30. A diameter of the cylindrical disposing bag 30 as opened into a complete round is greater than that of the second bag fraction 20B as opened into a complete round. The diameter of the cylindrical disposing bag 30 as opened is preferably greater than or equal to 40 mm for facilitating wrapping of the used tampon including the absorbent body 11 and the take-out code 12. More preferably, the diameter of the cylindrical disposing bag 30 is greater than or equal to 60 mm.

On the other hand, a length L1 is required to be greater than L2 of the length of the second bag fraction 20B in longitudinal direction. As shown in FIG. 2B and 3A, in the condition separated from the first bag fraction 20A, the cylindrical disposing bag 30 has to be projected from the second bag fraction 20B.

A length L0 between the laterally extending seal portions 23 and 24 of the packaging bag 20 is preferably longer than the overall length of the sanitary tampon 10 in a range of 20 to 50 mm. When the sanitary tampon 10 is regular size having the overall length of 120 mm, L0 is preferably 140 to 170 mm.

On the other hand, a longitudinal length of the first bag fraction 20A, namely a length L3 from the laterally extending seal portion 23 to the cutting portion 25 is preferably greater than the length of the outer cylinder 14 of the applicator 13. In case of the finger type sanitary tampon, in which the absorbent body 11 and the taker-out cord 12 without the applicator are packed, the length L3 is preferably longer than the overall length of the absorbent body 11.

In case of the regular sized sanitary tampon 10, the overall length of the outer cylinder 14 is about 70 mm. The length L3 of the first bag fraction 20A is greater than or equal to 70 mm. On the other hand, since the length of the absorbent body 11 is about 50 mm, the length L3 of the first bag fraction 20A is preferably greater than or equal to 50 mm, in case of the finger type sanitary tampon. In the case where the length L3 of the first bag fraction 20A falls within the range set forth above, when the first bag fraction 20A and the second bag fraction 20B are separated, the outer cylinder 14 and/or the absorbent body 11 is maintained within the first bag fraction 20A. Thus, the outer cylinder 14 and/or the absorbent body 11 can be maintained in sanitary conditions until being taken out from the first bag fraction 20A.

As shown in FIG. 3B, the cylindrical disposing bag 30 are folded with inwardly folded portions 30a, 30b, 30c and 30d to be made a dimension received within the packaging bag 20. A base end portion 33 of the cylindrical disposing bag 30 is heat sealed together with the package sheet 21 in a condition sandwiched by the package sheet 21 at the laterally extending seal portion 24, and secured to the end of the second bag fraction 20B. Such laterally extending seal portion 24 serves both for sealing the end of the packaging bag 20 and for securing the used substance disposing sheet 31. Therefore, it becomes unnecessary to separately provide securing means for securing the used substance disposing sheet 31 inside of the packaging bag 20.

As shown in FIG. 1, within the packaging bag 20, an opening portion 34 of the cylindrical disposing bag 30 extends into the first bag fraction 20A. The cylindrical disposing bag 30 is overlapped with parts of the inner cylinder 16 and the outer cylinder 14 of the applicator 13 in folded condition.

On the outer surface of the packaging bag 30 of the individual package 1, unpacking method is indicated by illustration and written sentence in a manner that the user may easily appreciate how to open the package. It is suggested to the user to grip the second bag fraction 20B by a dominant hand and grip the first bag fraction 20A by the other hand.

Normally, the first bag fraction 20A is held by the left hand and the second bag fraction 20B is held by the right hand as dominant hand. At this condition, pulling the first and second bag fractions in directions away from each other causes shearing of the packaging bag 20 along the cutting portion 25. When the package is opened, the first bag fraction 20A is held on the left hand with maintaining the outer cylinder 14 of the applicator 13, and the second bag fraction 20B is held on the right hand.

On the other hand, when the packaging bag 20 is cut along the cutting portion 25, the cylindrical disposing bag 30 secured to the second bag fraction 20B at the laterally extending seal portion 24 is pulled from the first bag fraction 20A. Thus, immediately after opening the packaging bag 20, the used substance disposing sheet 31 is held on the right hand as dominant hand. At this time, the opening portion 34 of the cylindrical disposing bag 30 is extended from the second bag fraction 20B, so that the cylindrical disposing bag 30 can be easily spread or stretched. Thus, the used tampon taken out from the user s body, i.e. vagina, can be immediately put within the cylindrical disposing bag 30. It should be noted that the user may grip the take-out cord 12 lead out of the user's body via the used substance disposing sheet 31 to take out the absorbent body 11 from the user's body, and then wrap the used tampon with the cylindrical disposing bag 30.

As set forth above, the used substance disposing sheet 31 has water absorbing function in the second layer 31b as an inner layer of the cylindrical disposing bag 30, and liquid blocking function in the first layer 31a as an outer layer of the cylindrical disposing bag 30. Therefore, when the absorbent body 11 is wrapped by the cylindrical disposing bag 30, menstrual blood exuding from the used tampon is absorbed by the second layer 31b to prevent menstrual blood from flowing out of the cylindrical disposing bag 30. Also, deposition of menstrual blood to the fingers can be successfully prevented.

It should be noted while the used tampon is wrapped in the used substance disposing sheet 31, the outer cylinder 14 of the non-use sanitary tampon 10 is held wrapped by the first bag fraction 20A. Therefore, contamination of the non-use outer cylinder can be successfully prevented to keep sanitary condition until the absorbent body 11 is inserted into vagina of the user by means of the applicator 13.

As will be appreciated as a matter of course, the applicator after use may also be wrapped with the cylindrical disposing bag 30 of the used substance disposing sheet 31.

Figure 4:
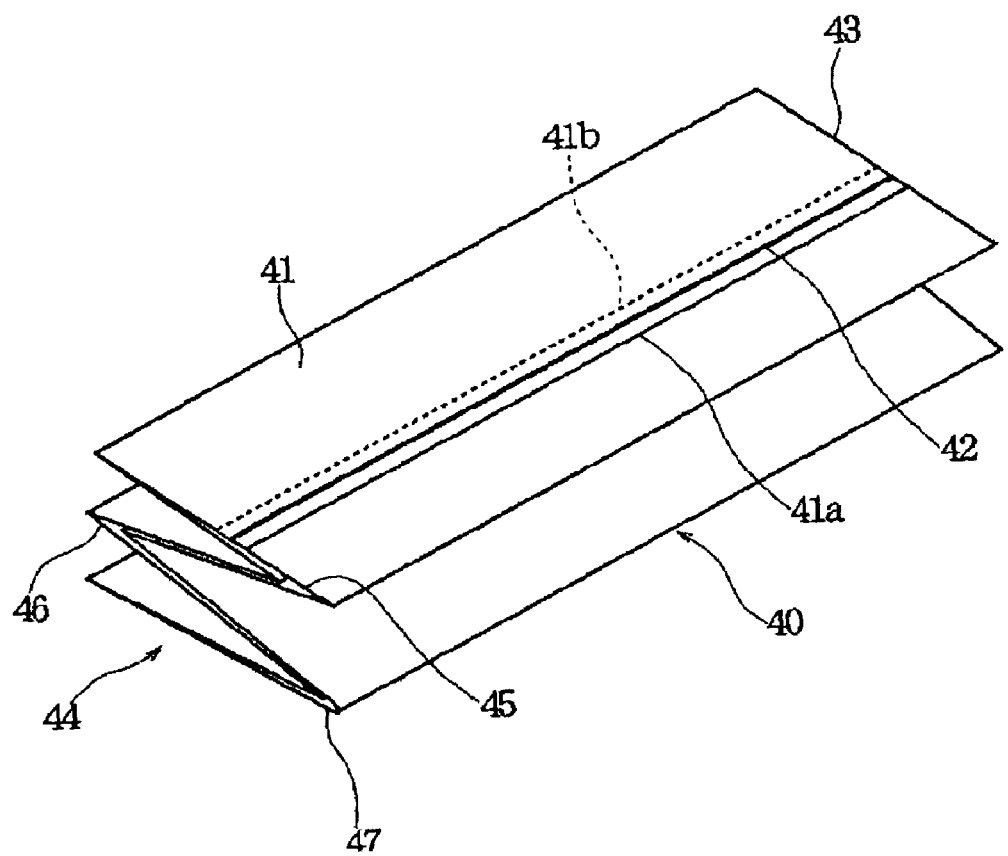
FIG. 4 is a perspective view showing a modification of the preferred embodiment showing a manner of folding the cylindrical disposing bag.

FIG. 4 is a perspective view showing only cylindrical disposing bag formed from a used substance disposing sheet showing a modification of the preferred embodiment shown in FIGS. 1 to 3B.

A cylindrical disposing bag 40 shown in FIG. 4 is formed from a used substance disposing sheet 41. The used substance disposing sheet 41 has the same structure as the used substance disposing sheet of the former embodiment, in which the cylindrical disposing bag 40 is consisted of an outer layer formed from a resin film and an inner layer formed from a fibrous structure having water absorbing function.

The used substance disposing sheet 41 is stacked at end edge portions 41a and 41b thereof and is heat sealed along a seal line 42 extending in a longitudinal direction in the stacked end edge portions 41a and 41b. The cylindrical disposing bag 40 is folded into flat rectangular shape and then folded into a W-shaped configuration along folding lines 45, 46, and 47. One base end portion 43 of the cylindrical disposing bag 40 is secured to the second bag fraction 20B of the packaging bag 20 at the laterally extending seal portion 24. Opening end portion 44 of the cylindrical disposing bag 40 is located within the first bag fraction 20A. Within the individual package, the cylindrical disposing bag 40 is received within the packaging bag 20. In the condition where the cylindrical disposing bag 40 is folded, the folded cylindrical disposing bag 40 is overlapped on the portion of the inner cylinder 16 of the applicator 13 of the sanitary tampon 10.

The packaging bag 20 is separated into the first and second bag fractions 20A and 20B along the cutting portion 25. The cylindrical disposing bag 40 shown in FIG. 4 is contained in the second bag fraction 20B in a manner similar to that in the former embodiment, and is extended from the second bag fraction 20B. By spreading the opening portion 44 of the cylindrical disposing bag 40, wide opening portion 44 of the cylindrical disposing bag 40 is formed to facilitate putting of the used tampon for disposal.

Figure 5:
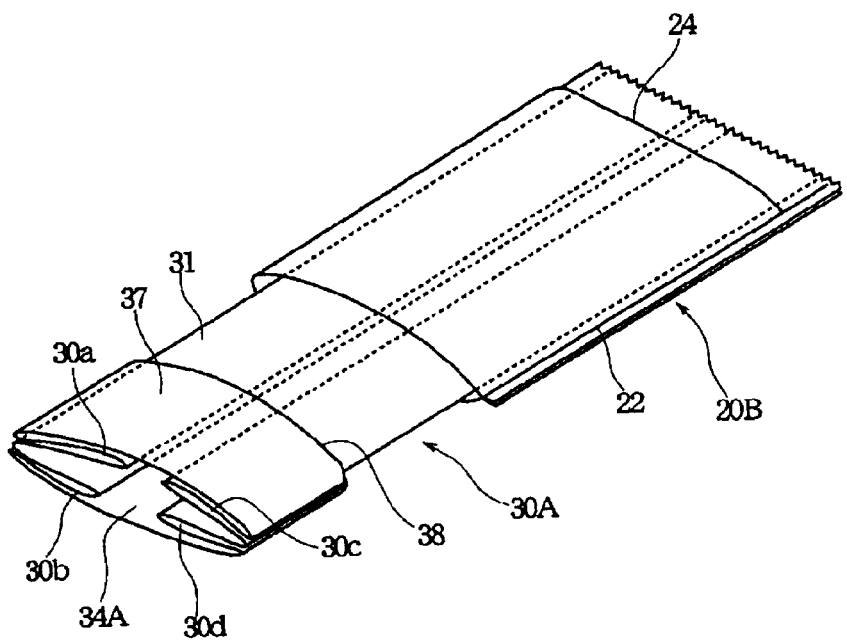
FIG. 5 is a perspective view showing an example, in which a pocket is formed in the cylindrical disposing bag.

FIG. 5 shows another modification of the embodiment shown in FIGS. 1 to 3.

In the modification shown in FIG. 5, the cylindrical disposing bag 30A is basically similar to the cylindrical disposing bag 30 shown in FIGS. 3A and 3B and has inwardly folded structure. In the modification shown in FIG. 5, in the opening portion of the cylindrical disposing bag 30A extending from the second bag fraction 20B, the used substance disposing sheet 31 is folded back outwardly to form a folded back portion 37. Then, the cylindrical disposing bag 30A is folded inwardly at the inwardly folded portions 30a, 30b, 30c and 30d in the condition where the folded back portion 37 is maintained.

Figure 6:
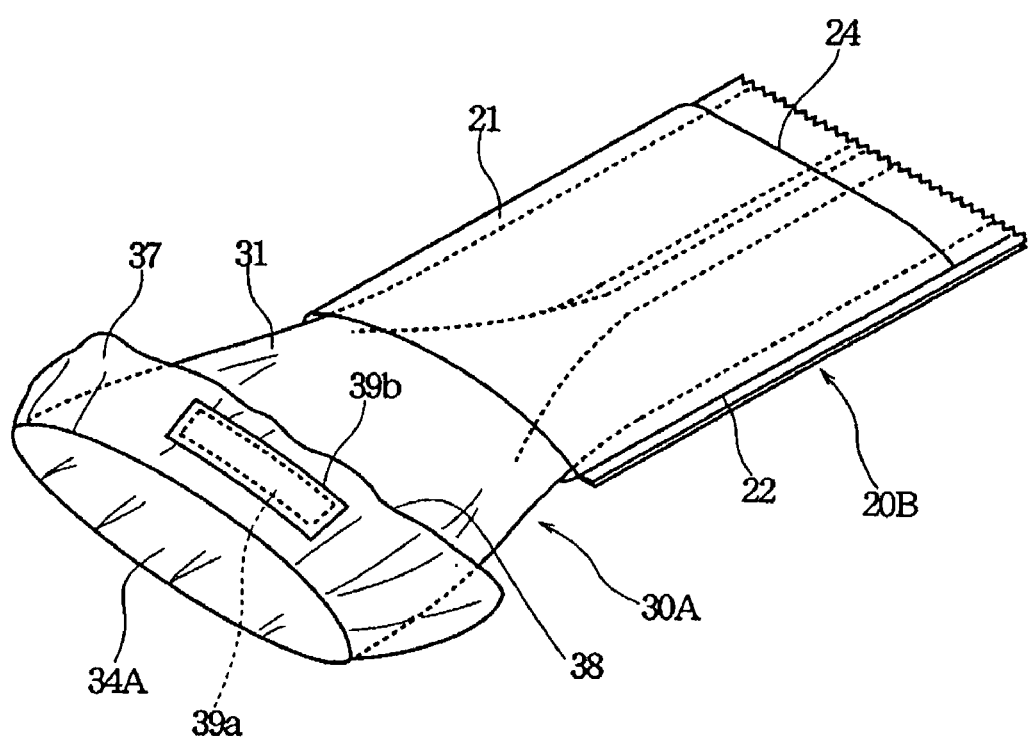
FIG. 6 is a perspective view showing the cylindrical disposing bag of FIG. 5 illustrated in developed form.

FIG. 6 shows the condition where the packaging bag 20 is separated into the first and second bag fractions 20A and 20B at the cutting portion 25 and the cylindrical disposing bag 30A is projected from the second bag fraction 20B with spreading an opening portion 34A. In the condition shown in FIG. 6, the opening portion 34A of the cylindrical disposing bag 30A is opened widely. In conjunction therewith, a finger pocket portion 38 is formed between the folded back portion 37 and the outer surface of the cylindrical disposing bag 30A around the opening portion 34A.

By using the used substance disposing sheet 31 in a form of the cylindrical disposing bag 31A, gripping of the take-out cord 12 extended from the absorbent body 11 and lead out from the user's body is facilitated. Namely, in the condition shown in FIG. 6, by inserting fingers into the finger pocket portion 38, the take-out cord 12 can be gripped to pull the absorbent body 11 out of the user's body. Upon gripping the take-out cord 12, the fingers may not be contaminated by menstrual blood deposited on the take-out cord 12. Then, by pulling the take-out cord 12, the absorbent body 11 pulled out of the user's body can be easily received within the cylindrical disposing bag 30A together with the take-out cord 12. In the condition where the used tampon, i.e. the used absorbent body 11 and the take-out cord 12, is received within the cylindrical disposing bag 30A, the folded back portion 37 is unfolded to extend frontwardly to enlarge an actual dimension of the cylindrical disposing bag 30A to ensure wrapping of the used tampon within the cylindrical disposing bag 30A.

Similarly to the former embodiment, the applicator used for inserting new tampon can also be wrapped by the cylindrical disposing bag 30A for disposal.

FIGS. 7A, 7B, 7C and 8A, 8B, 8C show another embodiment of a used substance disposing sheet and a cylindrical disposing bag formed by the used substance disposing sheet according to the present invention.

As shown in FIGS. 7A, 7B and 7C, a cylindrical disposing bag 50 is formed with a first used substance disposing sheet 51 and a second used substance disposing sheet 52. The first and second used substance disposing sheets 51 and 52 are mutually identical shape. The first used substance disposing sheet 51 has a first outer layer 51a formed from the resin film for fulfilling liquid blocking function and a second inner layer 51b formed from a fibrous structure having water absorbing function. The second used substance disposing sheet 52 also has a first outer layer 52a formed from the resin film and a second inner layer 52b formed from a fibrous structure having water absorbing function.

As shown in FIG. 7A, the first and second used substance disposing sheets 51 and 52 are placed in stacked condition with mating the second inner layers 51b and 52b. A folded back portion 51c at the tip end of the first used substance disposing sheet 51 is folded back along a folding line 51d to stack on the first outer layer 51a of the first used substance disposing sheet 51. Likewise, a folded back portion 52c at the tip end of the second used substance disposing sheet 52 is also folded back along a folding line 52d to stack on the first outer layer 52a of the second used substance disposing sheet 52.

Then, as shown in FIG. 7B, the first used substance disposing sheet 51 and the second used substance disposing sheet 52 are heat sealed along seal portions 53 and 54 to form the cylindrical disposing bag 50. At this time, the first and second used substance disposing sheets 51 and 52 are stacked with maintaining the folded back portion 51c stacked on the first outer layer 51a and the folded back portion 52c stacked on the first outer layer 52a. At this condition, both side edges of the stacked portion of the folded back portion 51c and the first outer layer 51a and side edges of the stacked portion of the folded back portion 52c and the first outer layer 52a are heat sealed along the seal portions 53 and 54.

The cylindrical disposing bag 50 has a base end portion 55 having small outer shape. As shown in FIG. 7C, the base end portion 55 is placed within the second bag fraction 20B. The base end portion is sealed together with the package sheet 21 at the laterally extending seal portion 24. Thus, the cylindrical disposing bag 50 is fixed to the second bag fraction 20B. The cylindrical disposing bag 50 is gradually widened from the base end portion 55. Accordingly, as shown in FIG. 7C, the cylindrical disposing bag 50 is partially folded at the widened portions to be received within the packaging bag 20 in the condition stacked with the sanitary tampon 10.

Since the cylindrical disposing bag 50 is formed to have wider width in an opening portion 56, the opening portion 56 of the cylindrical disposing bag 50 are opened widely for use as shown in FIG. 8A, in the condition where the packaging bag 20 is sheared into the first and second bag fractions 20A and 20B along the cutting portion 25. At this time, the folded back portions 51c and 52c folded outwardly to define a finger pocket portion 57 together with the outer surface of the cylindrical disposing bag 50. By inserting fingers into the finger pocket portion 57, the take-out cord 12 can be gripped to pull the absorbent body 11 out of the user's body. Upon gripping the take-out cord 12, the fingers may not be contaminated by menstrual blood deposited on the take-out cord 12. Then, by pulling the take-out cord 12, the absorbent body 11 pulled out of the user's body can be received within the cylindrical disposing bag 50 together with the take-out cord 12 as shown in FIG. 8A.

It is also possible to insert fingers of one hand into the finger pocket portion 57, and to grip the take-out cord 12 by the fingers of the other hand to pull out the absorbent body 11 from the user's body, thereby directly gripping the pulled out used absorbent body 11 by the opening portion 56 of the cylindrical disposing bag 50 for receiving the absorbent body 11 within the cylindrical disposing bag 50. In this case, the absorbent body 11 is received in opposite orientation to that illustrated in FIGS. 8A and 8C, namely with placing absorbent body 11 on the side of the laterally extending seal portion 24.

As set forth above, after receiving the absorbent body 11 and the take-out cord 12 within the cylindrical disposing bag 50, the folded back portion 51c is unfolded as shown by arrow (i) of FIG. 8A and the folded back portion 51c is further folded to be placed over the folded back portion 52c of the second used substance disposing sheet 52 for closing the opening portion 56 of the cylindrical disposing bag 50 in the condition of receiving the absorbent body 11 and the take-out cord 12. Thus, external exuding of menstrual blood from the cylindrical disposing bag 50 can be successfully prevented.

On the other hand, in the embodiment shown in FIGS. 7A to 8C, it is possible to provide the folded back portion 51c only in one used substance disposing sheet, e.g. the first used substance disposing sheet 51, and the folded back portion 52c of the second used substance disposing sheet 52 (as another used substance disposing sheet) may be eliminated. Even with such construction, after receiving the used absorbent body 11 and the take-out cord 12 within the cylindrical disposing bag, by folding the folded back portion 51c over the outer surface of the first outer layer 52a of the second used substance disposing sheet 52, the opening portion 56 can be closed in the same condition as that illustrated in FIG. 8B.

On the other hand, in respective of the cylindrical disposing bag 30 shown in FIGS. 2B, 3A and 3B, the cylindrical disposing bag 40 shown in FIG. 4, the cylindrical disposing bag 30A shown in FIGS. 5 and 6 and the cylindrical disposing bag 50 shown in FIGS. 7A–8C, it is possible to provide fastening means for maintaining the opening portion in closed condition after receiving the absorbent body 11 and the take-out cord 12.

As the fastening means, for example, in case of the cylindrical disposing bag 30A shown in FIG. 6, on one or more portions of externally oriented surface of the folded back portion 37, a pressure sensitive adhesive layer 39a is provided. The pressure sensitive adhesive layer 39a is covered by a release sheet 39b for protection. After putting the used tampon into the cylindrical disposing bag 30A, the release sheet 39b is removed to expose an adhesive surface. Then, by adhering the adhesive layer 39a on the used substance disposing sheet forming the cylindrical disposing bag 30A, the opening portion of the cylindrical disposing bag can be closed.

On the other hand, as the fastening means, in case of the cylindrical disposing bag 50 shown in FIGS. 8A, 8B and 8C, a fastening tape 59 is provided on the inner surface of one of the folded back portion 51c, namely on the surface opposing the first outer layer 51a. The fastening tape 59 is fixed on the inner surface of the folded back portion 51c at a fixed portion 59a on one portion and is provided with the pressure sensitive adhesive layer at an adhering portion 59b on the other portion. The adhering portion 59b is held in folded condition.

After receiving the used tampon within the cylindrical disposing bag 50 and folding the folded back portion 51c over the folded back portion 52c, the adhering portion 59b of the fastening tape 59 can be adhered on the surface of the first outer layer 52a of the second used substance disposing sheet 52 to firmly close the opening portion 56.

The fastening means employing the pressure sensitive adhesive layer 39a and/or the fastening tape 59 may be selectively applicable for the cylindrical disposing bags 30, 30A, 40, 50, respectively.

As will be appreciated as a matter of course, the applicator after use may also be wrapped with the cylindrical disposing bag 50 of the used substance disposing sheet.

Figure 10A:
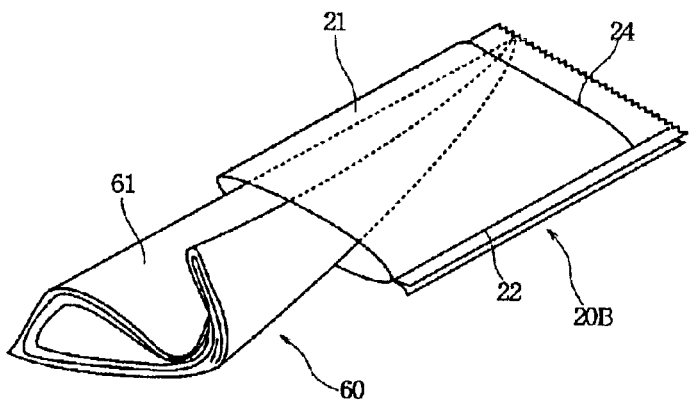
FIG. 10A is a perspective view showing a condition where the folded used substance disposing sheet is coupled with inside of the second bag fraction.
Figure 10B:
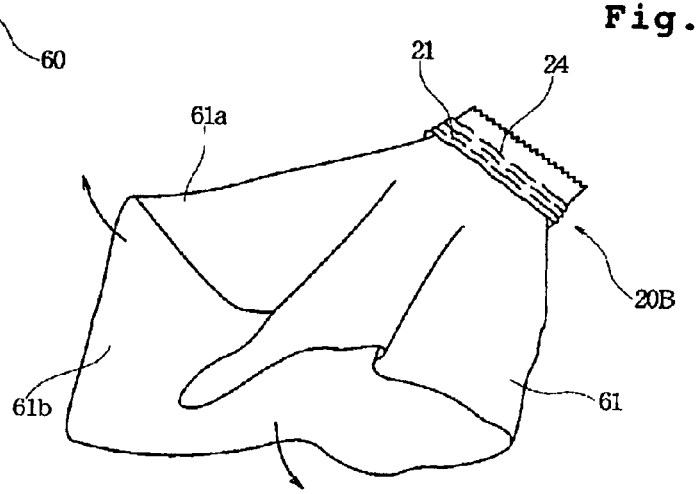
FIG. 10B is a perspective view showing the used substance disposing sheet in developed condition.

FIGS. 9A, 9B, 9C and 10A, 10B show another embodiment of the present invention, in which FIGS. 9A to 9C show folding process of the used substance disposing sheet, FIG. 10A shows a condition where the folded processed sheet is received in the second bag fraction, and FIG. 10B shows a condition where the used substance disposing sheet is developed.

A used substance disposing sheet 61 shown in FIG. 9A is a square shape having a length in one edge greater than or equal to 50 mm, and more preferably greater than or equal to 80 mm. In the used substance disposing sheet 61 in the shown orientation, the lower layer is the resin sheet layer forming the first outer layer 61a and having the liquid blocking function, and the upper layer is formed from the fibrous structure having water absorbing function and forming a second inner layer 61b.

With taking a geometrical center of the used substance disposing sheet 61 shown in FIG. 9A as a folding center 62, a first folding line 63 and a second folding line 64 mutually intersecting at the folding center 62 are set. Then, the used substance disposing sheet 61 is folded along the first folding line 63 inwardly orienting the second inner layer 61b having water absorbing function. Subsequently, the used substance disposing sheet 61 is folded along the second folding line 64 to form folded four ply used substance disposing sheet as shown in FIG. 9B.

The folded used substance disposing sheet 61 shown in FIG. 9B is further folded along a third folding line 65 extending diagonally across the folding center 62 to form a triangular folded sheet 60 as shown in FIG. 9C.

As shown in FIG. 10A, the folded sheet 60 is further folded to be received within the packaging bag 20. The folding center 62 of the used substance disposing sheet 61 or a portion in the vicinity of the folding center 62 is sealed together with the package sheet 21 along the laterally extending seal portion 24 so that the used substance disposing sheet can be fixed to the packaging bag 20. Within the packaging bag 20, the used substance disposing sheet 61 folded as shown in FIG. 10A is received within a space defined between the inner cylinder 16 of the applicator 13 and the package sheet 21.

Upon opening the individual package, the packaging bag 20 is separated into the first and second bag fractions 20A and 20B along the cutting portion 25. At this time, as shown in FIG. 10A, the used substance disposing sheet 61 is extended outside of the second bag fraction 20B. For unfolding the used substance disposing sheet 61 as shown in FIG. 10B, the package sheet 21 forming the second bag fraction 20B is rolled up toward the laterally extending seal portion 24 to permit the used substance disposing sheet 61 to be unfolded or developed as shown.

Touching the fingers on the surface of the first outer layer 61a formed from the resin film of the used substance disposing sheet 61, the take-out cord 12 lead out of the user's body is gripped with the second inner layer 61b having water absorbing function to pull out the absorbent body 11. It is also possible to wrap the used absorbent body 11 taken out from the user's body with orienting the second inner layer 61b inside.

It should be noted that, in the embodiments shown in FIGS. 2B, 5, 6, 7C, after cutting the packaging bag 20, the package sheet 21 forming the second bag fraction 20B is rolled up toward the laterally extending seal portion 24, so that the used substance disposing sheets 31, 51, 52 in cylindrical form can be spread or stretched widely.

As will be appreciated as a matter of course, the applicator after use may also be wrapped with the folded sheet 60 of the used substance disposing sheet 61.

Figure 11:
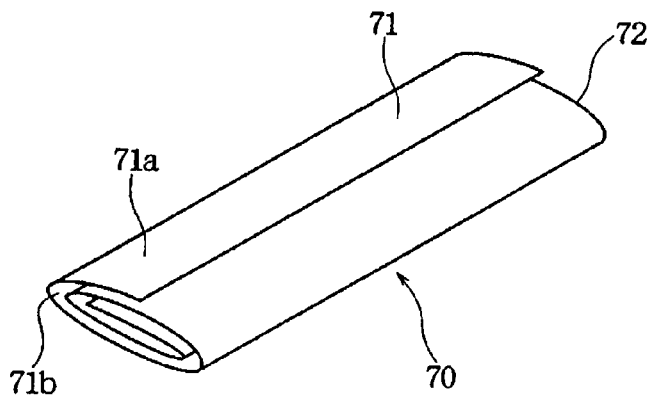
FIG. 11 is a perspective view showing a condition where the used substance disposing sheet is rolled.

FIG. 11 shows a further embodiment of the present invention.

A used substance disposing sheet 71 shown in FIG. 11 is formed with a first outer layer 71a formed from the resin film and a second inner layer 71b formed from the fibrous structure having water absorbing function. The used substance disposing sheet 71 is formed into square or rectangular shape in developed condition. The used substance disposing sheet 71 is rolled with placing the second inner layer 71b inside to form a rolled used substance disposing sheet 70. The rolled used substance disposing sheet 70 is received within the packaging bag 20 shown in FIG. 1. A base end portion 72 of the rolled used substance disposing sheet 70 is sealed together with the package sheet 21 at the laterally extending seal portion 24.

The packaging bag 20 containing the used substance disposing sheet 71 therein is separated at the cutting portion 25. Then, the rolled used substance disposing sheet 70 is projected from the second bag fraction 20B. Similarly to that shown in FIG. 10B, the package sheet 21 forming the second bag fraction 20B is rolled up toward the laterally extending seal portion 24. The used substance disposing sheet 71 can be spread or stretched widely to easily receive the used tampon.

For the used substance disposing sheet 61 shown in FIGS. 9A to 10B and the used substance disposing sheet 71 shown in FIG. 11, the fastening means of the pressure sensitive adhesive layer 39a shown in FIG. 6 or the fastening tape 59 shown in FIG. 8 may be provided.

As will be appreciated as a matter of course, the applicator after use may also be wrapped with the rolled used substance disposing sheet 70 of the used substance disposing sheet 71.

Figure 12:
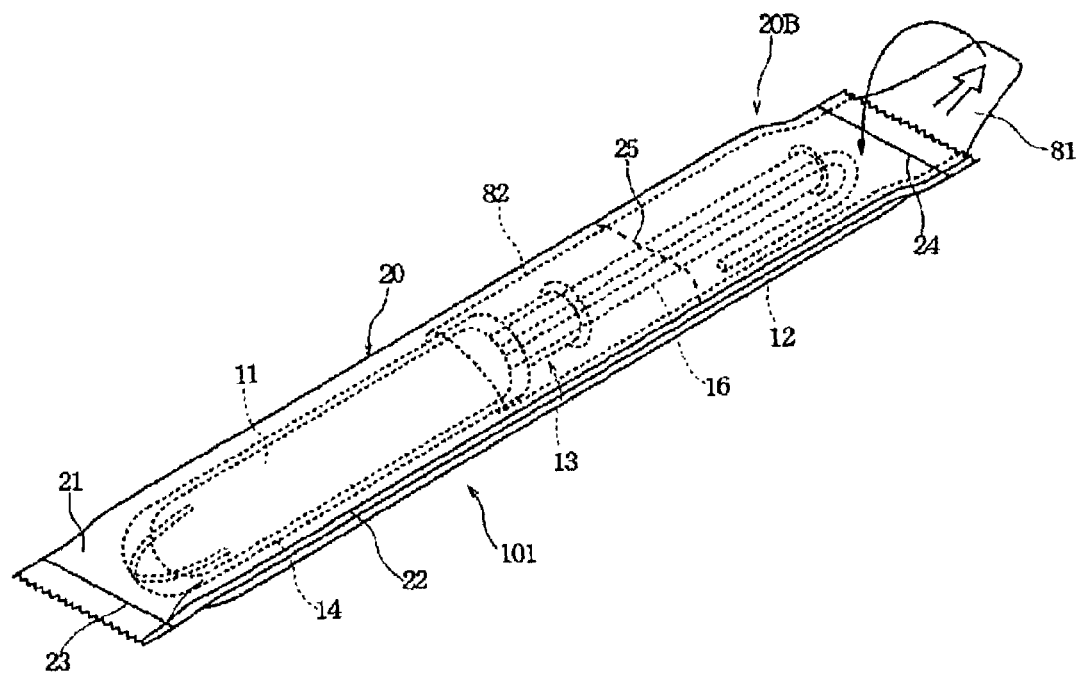
FIG. 12 is a perspective view showing a structure of another embodiment of the individual package.
Figure 13:
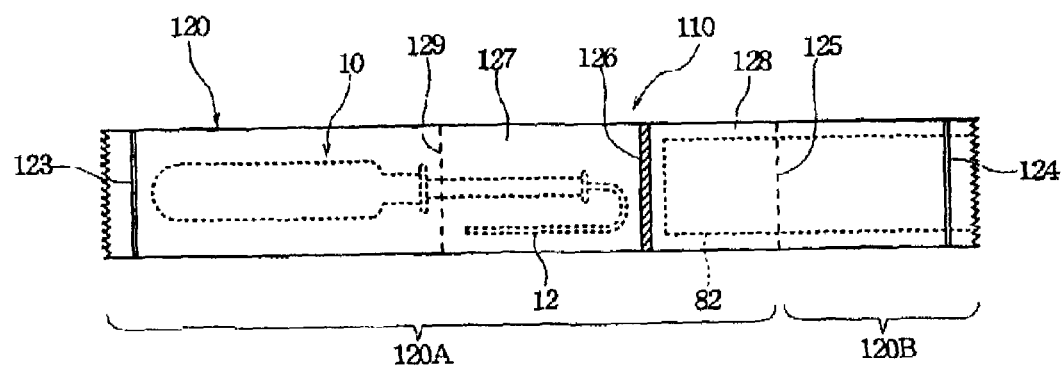
FIG. 13 is a perspective view showing a structure of further embodiment of the individual package.

FIGS. 12 and 13 show an embodiment having different basic structure of the individual package from that shown in FIG. 1.

The packaging bag 20 of an individual package 101 shown in FIG. 12 is formed into longitudinally elongated form with the package sheet 21. The packaging bag 20 is separated into the first and second bag fractions 20A and 20B at the cutting portion 25. Within the second bag fraction 20B, a used substance disposing sheet 82 is received. The used substance disposing sheet 82 is selected among any one of the used substance disposing sheets shown in FIGS. 1 to 11.

In the embodiment shown in FIG. 12, a pulling tab 81 is provided at the end portion of the second bag fraction 20B of the packaging bag 20, which is fixed at the laterally extending seal portion 24. Before opening the individual package, the pulling tab 81 is bent to abut onto the outer surface of the package sheet 21 forming the packaging bag 20 of the individual package 101 and is lightly adhered on the outer surface of the package sheet 21 in a manner to be easily peeled off. Upon unpacking, the pulling tab 81 is peeled off the outer surface of the package sheet 21 and is gripped to be pulled for trigger shearing at the cutting portion 25 to separate the second bag fraction 20B from the first bag fraction 20A.

In the embodiment shown in FIG. 13, a packaging bag 120 forming an individual package 110 is formed with the package sheet 21 similar to the former embodiment. The individual package 110 has longitudinally extending seal portion (not shown) and laterally extending seal portions 123 and 124 to form into longitudinally extending form. The inside of the packaging bag 120 is separated into a first storage space 127 and a second storage space 128 by a seal portion 126 formed at the intermediate position in the longitudinal direction. Within the first storage space 127, the sanitary tampon 10 is received. Within the second storage space 128, the used substance disposing sheet 82 is received. The used substance disposing sheet 82 is fixed on the inner surface of the package sheet at the laterally extending seal portion 124.

In the first storage space 127, a first cutting portion 129 formed with perforation is formed for shearing into front part and rear part. Similarly, in the second storage space 128, a second cutting portion 125 formed with perforation is formed for shearing into front part and rear part.

In this embodiment, a first bag fraction 120A is defined between the laterally extending seal portion 123 of the packaging bag 120 and the second cutting portion 125. A second bag fraction 120B is defined between the second cutting portion 125 and the laterally extending seal portion 124.

In the shown embodiment, the individual package 110 is initially sheared at the second cutting portion 125 to separate the packaging bag 120 into the first and second bag fractions 120A and 120B. Thus, the second bag fraction 120B is separated from the first bag fraction 120A. At this time, the used substance disposing sheet 82 is extended from the second bag fraction 120B. The used substance disposing sheet 82 is selected among any one of the used substance disposing sheets shown in FIGS. 1 to 11. By using the used substance disposing sheet 82, the absorbent body 11 is taken out from the user's body, and is wrapped for disposal. At this time, since the first storage space 127 is not opened, the sanitary tampon 10 can be protected from external contamination.

After wrapping the used tampon with the used substance disposing sheet 82, the package sheet is sheared at the first cutting portion 129 to open the first storage space to take out new sanitary tampon 10 therefrom to insert into the user's body, i.e. vagina.

In the shown embodiment, while the used tampon is taken out and is wrapped with the used substance disposing sheet 82, non-use sanitary tampon 10 is maintained in sealed condition within the first storage space 127. Therefore, the non-use sanitary tampon 10 can be held in sanitary condition.

It should be noted that the individual package may pack the finger type body fluid absorbent article consisted of the absorbent body 11 and the take-out cord 12, and not including the applicator.

With the present invention, when the individual package is opened by shearing the package sheet, since the used substance disposing sheet is fixed on the opened bag fraction, the user may obtain the used substance disposing sheet for instantly wrap the used tampon taken out from the user's body. On the other hand, since the used substance disposing sheet is projected from the separated bag fraction, the used substance disposing sheet may be widely stretched to facilitate wrapping of the tampon including the absorbent body and the take-out cord. In addition, the applicator used for insertion of brand-new tampon may also be wrapped with the used substance disposing sheet.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An individual package of a body fluid absorbent article, individually packing said body fluid absorbent article, comprising:
    an absorbent body to be inserted into a vagina with a package sheet in a form of a packaging bag;
    a used substance disposing sheet for wrapping a used absorbent body taken out from a user's body for disposal, being packed within said packaging bag together with said body fluid absorbent article, wherein
    said package sheet is provided with a cutting portion for separating said packaging bag into bag fractions, and a part of said used substance disposing sheet being fixed to one of said bag fractions,
    wherein said packaging bag is a longitudinally elongated shape, said packaging bag is provided with said cutting portion for separating into a first bag fraction and a second bag fraction, and said used substance disposing sheet is fixed inside of said second bag fraction and extended from said second bag fraction, and
    wherein said used substance disposing sheet is welded together with said package sheet in a condition sandwiched by said package sheet at a longitudinal end of said second bag fraction.

2. An individual package of a body fluid absorbent article as set forth in claim 1, wherein said body fluid absorbent article includes said absorbent body and a take-out cord extending from a rear end of said absorbent body, said absorbent body is contained in said first bag fraction.

3. An individual package of a body fluid absorbent article as set forth in claim 1, wherein said body fluid absorbent article includes said absorbent body, a take-out cord extending from a rear end of said absorbent body and an applicator having an outer cylinder receiving therein said absorbent body and an inner cylinder along which said take-out cord is inserted, and which is inserted into said outer cylinder for pushing said absorbent body out of said outer cylinder, and said outer cylinder is contained in said first bag fraction.

4. An individual package of a body fluid absorbent article as set forth in claim 1, wherein said used substance disposing sheet is formed into a cylindrical disposing bag.

5. An individual package of a body fluid absorbent article as set forth in claim 1, wherein said packaging bag defines a space for receiving said body fluid absorbent article, and a space separated from the former space and receiving said used substance disposing sheet.

6. An individual package of a body fluid absorbent article as set forth in claim 1, wherein said used substance disposing sheet has a liquid blocking function.

7. An individual package of a body fluid absorbent article as set forth in claim 1, which further includes fastening means for retaining said used substance disposing sheet wrapping the used absorbent body in closed condition.

8. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging bag together with said body fluid absorbent article, wherein said package sheet is provided with a cutting portion for separating said packaging bag into bag fractions, and a part of said used substance disposing sheet being fixed to one of said bag fractions, wherein said used substance disposing sheet is formed into a cylindrical disposing bag, and a diameter of said cylindrical disposing bag as stretched is greater than a diameter of said second bag fraction, and said cylindrical disposing bag is received within said packaging bag in folded condition.

9. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging bag together with said body fluid absorbent article, wherein said package sheet is provided with a cutting portion for separating said packaging bag into bag fractions, and a part of said used substance disposing sheet being fixed to one of said bag fractions, wherein said used substance disposing sheet is formed into a cylindrical disposing bag, and said cylindrical disposing bag has a diameter at an opening portion of said cylindrical disposing bag extending from said second bag fraction, greater than a diameter of a portion positioned within said second bag fraction.

10. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging bag together with said body fluid absorbent article, wherein said package sheet is provided with a cutting portion for separating said packaging bag into bag fractions, and a part of said used substance disposing sheet being fixed to one of said bag fractions, wherein said used substance disposing sheet is formed into a cylindrical disposing bag, and said cylindrical disposing bag extending from said second bag fraction, has a folded back portion folded outwardly at the opening portion for defining a finger pocket portion defined between said folded back portion and an outer surface of said cylindrical disposing bag.

11. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging bag together with said body fluid absorbent article, wherein said package sheet is provided with a cutting portion for separating said packaging bag into bag fractions, and a part of said used substance disposing sheet being fixed to one of said bag fractions, and wherein said used substance disposing sheet is folded along folding lines radially extending from an arbitrarily set folding center, and said used substance disposing sheet is fixed onto an inner surface of said package sheet at said folding center or a portion in the vicinity of said folding center.

12. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging bag together with said body fluid absorbent article, wherein said package sheet is provided with a cutting portion for separating said packaging bag into bag fractions, and a part of said used substance disposing sheet being fixed to one of said bag fractions, and wherein said used substance disposing sheet is rolled and a part of said rolled used substance disposing sheet is fixed onto an inner surface of said package sheet.

13. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging bag together with said body fluid absorbent article, wherein said package sheet is provided with a cutting portion for separating said packaging bag into bag fractions, and a part of said used substance disposing sheet being fixed to one of said bag fractions, wherein said used substance disposing sheet has a liquid blocking function, and one surface side of said used substance disposing sheet is formed with a fibrous structure having water absorbing function.

14. An individual package of a body fluid absorbent article, individually packing said body fluid absorbent article comprising:

an absorbent body to be inserted into a vagina with a package sheet in a form of a packaging bag;

a used substance disposing sheet for wrapping a used absorbent body taken out from a user's body for disposal, being packed within said packaging baa together with said body fluid absorbent article, wherein said package sheet is provided with a cutting portion for separating said packaging bag into bag fractions, and a part of said used substance disposing sheet being fixed to one of said bag fractions, said used substance disposing sheet is formed into a cylindrical disposing bag, and said used substance disposing sheet has a liquid blocking function and has a fibrous structure having water absorbing function formed on one surface side.

* * * * *